United States Patent [19]
Jones et al.

[11] Patent Number: 4,884,438
[45] Date of Patent: Dec. 5, 1989

[54] METHOD AND APPARATUS FOR MEASURING FLUID FLOW PARAMETERS THROUGH NATURALLY FRACTURED MEDIA

[75] Inventors: Timothy A. Jones, Carrollton; Thomas J. Kaluza; Robert E. Roach, both of Dallas, all of Tex.

[73] Assignee: Mobil Oil Corporation, New York, N.Y.

[21] Appl. No.: 260,350

[22] Filed: Oct. 20, 1988

[51] Int. Cl.$^4$ .............................................. E21B 49/00
[52] U.S. Cl. ......................................... 73/153; 73/38
[58] Field of Search ................... 73/38, 151, 153, 813, 73/821

[56] References Cited

U.S. PATENT DOCUMENTS

| | | | |
|---|---|---|---|
| 2,705,418 | 4/1955 | Reichertz et al. | 73/38 |
| 3,162,037 | 12/1964 | Hurst | 73/38 |
| 4,233,840 | 11/1980 | Goss et al. | 73/153 |
| 4,599,891 | 7/1986 | Brauer et al. | 73/38 |

OTHER PUBLICATIONS

Muskat, Morris, Ph.D, "Physical Principles of Oil Production", McGraw-Hill Book Company, Inc., 1949, pp. 246–250.

Primary Examiner—Stewart J. Levy
Assistant Examiner—Kevin D. O'Shea
Attorney, Agent, or Firm—Alexander J. McKillop; Charles J. Speciale; Michael J. Mlotkowski

[57] ABSTRACT

A method and apparatus for determining certain fluid flow parameters for naturally fractured media. Specifically provided is a method and apparatus to measure the flow rate, pressure drop, fracture aperture, fluid supply temperature and sample-loading force. A naturally fractured media core sample is obtained for testing and cut into a pair of core blocks having mating fractured forces. The fracture face of the core sample prepared in this manner, yields a more representative surface for flow study, eliminating the problem arising from the fact that most fractures cut across round core samples, resulting in an unnatural, elliptical surface for evaluation. A flow cell assembly is provided to receive the pair of core blocks and secure them during the measurement operation. The flow cell assembly permits adjustment of the fracture aperture to facilitate comprehensive evaluation.

35 Claims, 7 Drawing Sheets

METHOD AND APPARATUS FOR MEASURING FLUID FLOW PARAMETERS THROUGH NATURALLY FRACTURED MEDIA

BACKGROUND OF THE INVENTION

The present invention relates to a method and apparatus for determining certain fluid flow parameters for naturally fractured media. In particular, a method and apparatus are provided whereby flow characteristics can be assessed at several fracture apertures within such media so that the impact of the fracture aperture on fluid flow may be accurately determined for reservoir modeling purposes.

In the production of oil, gas and other minerals, certain properties of the subterranean reservoir must be determined. Two of the key, most commonly measured properties are the porosity and permeability of the reservoir. The porosity of a material is the ratio of the aggregate volume of its void or pore spaces (i.e., pore volume) to its gross bulk volume and, in the case of an oil or gas reservoir, is a measure of the capacity within the reservoir rock which is available for storing oil or gas. The permeability of a material is a measure of the ability of the material to transmit fluids through its pore spaces and is inversely proportional to the flow resistance offered by the material. Additionally, fractures play an important role in reservoir behavior. Fractures have the ability to either enhance or restrict fluid flow in reservoirs and can alter the apparent permeability and/or porosity of the rock. Because of these important influences, the ability of fractures to conduct fluids must be fully understood in order to accurately model and effectively engineer a given reservoir.

Porosity and permeability are determined by taking core samples from the reservoir site and carrying out well-defined measurement techniques on the samples. There are several techniques available for making such measurements, many of which are described in Petroleum Production Engineering Development by L. C. Uren, Fourth Edition, McGraw-Hill Book Company, Inc., 1956, pps 660-669. Another standard reference for core sample analysis is the API Recommended Practice for Core-Analysis Procedure, API RP40, American Petroleum Institute, 1960, 55 pps. While these procedures are suitable for measuring the porosity and permeability of a sample, they do not address techniques capable of adequately assessing the contribution of reservoir fractures to overall production.

All reservoirs are probably fractured to some extent. Reservoir fracture systems are often complicated, interconnected arrays of fluid flow paths. However, flow in the simplest case, a single fracture, must be analyzed before an array can be studied. Flow in a single fracture has been traditionally characterized by the so-called Cubic law equation. This equation was developed for the case where steady-state isothermal, laminar flow between two parallel smooth plates exists.

Flow between parallel plates is an idealized case of single-phase flow and can not adequately represent all cases of flow in fractures. While the Cubic law relationship can represent laminar flow for viscous incompressible liquids in fractures of moderate size reasonably well, natural fractures behave quite differently from idealized, smooth surfaces when very narrow fractures are considered. Since the walls of natural rock fractures are not smooth and parallel, a method and apparatus useful in conducting tests to determine the impact of natural fractures on fluid flow is required.

Analogising the flow through fractures to the work conducted for pipe flow by L. F. Moody and reported in "Friction Factors for Pipe Flow", Transactions of ASME, 66, (1944), pps. 671–684, has been found to be useful. In Moody's work, a friction factor was developed for use in the calculation of pressure drop. The friction factor provides a measure of the resistance to flow caused by fluid drag on the surface and by internal mixing and is a dimensionless number. Another key factor, the Reynolds number, provides a dimensionless term representative of mass flow. The critical Reynolds number is that number at which flow changes from laminar to turbulent. Friction factors for turbulent flow are dependent upon the relative roughness of the pipe. In the turbulent flow regime, the rougher the pipe, the higher the friction factor. For laminar flow in pipes, the friction factor is not a function of surface roughness.

With regard to flow in fractures, friction factors can be used to account for the increase in pressure drop caused by fracture surface roughness. Through the use of pipe flow analogy, a modified Cubic law equation can be developed which avoids the smooth prallel plate assumption and is useful in the study of natural fracture phenomena. This equation will be correct for all single-phase, open fracture laminar and turbulent flow calculations, provided the correct friction factor is used. Friction factors may be developed experimentally using the method and apparatus of the present invention.

As stated by L. H. Reiss in "The Reservoir Engineering Aspects of Fractured Formations", Gulf Publishing Co., Houston, Tex., 1980, 108 pps., Darcy's law is relatable to fracture flow for the case of smooth parallel plate flow. Additionally, as was the case for the Cubic law, Darcy's law may also be modified to account for rough surfaces, as long as the correct friction factor is used.

Various past studies have experimentally determined critical Reynolds numbers for viscous flow in fractured media. The range of reported results vary by a factor of four from the low to high value depending on the investigator. Surface roughness is believed responsible for this variance in findings, as well as the inherent instability of the transition zone between laminar and turbulent flow. For rough fractures, the critical Reynolds number decreases as fracture aperture decreases; that is, turbulent flow in small fractures will occur at lower velocities than previously expected. Normally, liquid flow in reservoirs is assumed to be laminar because of low fluid velocity; however, since fractures have high permeabilities, fluid velocities in reservoir fractures may reach the critical value in rough fractures.

As indicated, reservoir modeling of fractured reservoirs is clearly enhanced by accurate knowledge of the fracture surface roughness characteristics present in an oil field. Surface roughness may be accounted for in modeling by the friction fractor, itself a function of the Reynolds number flow parameter and the surface roughness to fracture aperture ratio (e/b), values all found to be highly reservoir fracture specific. While it is known in the art to manufacture fracture surfaces by gluing grains of sand to a smooth surface or by sawing a portion of a core sample in half, as done by Hurst in U.S. Pat. No. 3,162,037, reservoir modeling is enhanced through the use of natural fractures in flow characterization work.

SUMMARY OF THE INVENTION

The present invention provides a method and an apparatus for determining certain fluid flow parameters for naturally fractured media. Specifically, the present invention provides a method and an apparatus which can measure the flow rate, pressure drop, fracture aperture, fluid temperature and sample-loading force. From the values measured, the friction factor and Reynolds number for a particular run may be determined. The flow cell apparatus provided permits the fracture aperture to be varied easily so that key flow parameters may accurately be assessed.

Structurally, the flow cell apparatus consists of a core mounting assembly adapted to enable the study of flow characteristics for a pair of substantially rectangular core block samples having mating, naturally fractured faces. The rectangular fracture face yields a more representative surface for flow study and eliminates the problem which arises due to the fact that most fractures cut across round core samples, resulting in an unnatural, eliptical surface for evaluation. However, the use of rectangular cores greatly alters the design of the flow cell, and increases the problem of sealing against leakage. The core mounting assembly of the present invention consists of a means for mounting the core sample blocks, and inlet and outlet end blocks having surfaces suitable for creating a seal when brought in contact with the core sample block mounting means. The core mounting assembly is installed within a flow cell housing utilizing suitable gaskets to permit leak-free operation. The flow cell housing is adapted to permit adjustment of the fracture aperture. Means to apply a preload to the core sample blocks for test purposes is also furnished. Two load cells are provided to monitor the value of the force acting on the core sample blocks.

When assembled, the inlet and outlet ports are axially aligned, with the centers of the ports also substantially aligned with the fracture aperture. This arrangement facilitates an extremely accurate, in-situ measurement of the fracture aperture using a long distance microscope and camera. To determine the average value of the fracture aperture, several pictures are taken at both ends of the flow cell apparatus, blown-up to provide an accurate view and averaged to obtain a single value for the aperture. To assure that any change in the aperture during testing is accounted for, linear variable differential transformers (LVDTs) are provided to monitor the fracture face spacing.

In addition to the flow cell assembly, the other main parts of the test apparatus include the fluid supply system, measuring system and the data acquisition and computation system.

Also, this invention furnishes a method for determining certain fluid flow parameters using naturally fractured media. A pair of rectangular blocks are cut from a cylindrical, naturally fractured core, so that the natural fracture is centered and provides mating fracture faces for flow study. The blocks are mounted within the flow cell apparatus described herein, with the fracture aperture set as desired. The test fluid is introduced under pressure through the inlet port of the flow cell apparatus and exits through the outlet port, with the flow rate and pressure drop monitored. The method, in a more comprehensive form, utilizes a series of tests conducted at several flow rates for a given aperture setting, with these series of tests then repeated at several aperture settings to more fully define the flow characteristics of a particular fracture surface.

Single-phase test fluids of varied viscosity and density are useful in this method to compare the resultant differences in flow characteristics. The method of this invention is also useful in the characterization of two-phase flow in natural fractures. Fracture surface roughness and the fluid properties themselves are among the controlling factors in characterizing two-phase flow. The method and apparatus also finds utility in the development of relative permeability curves for two-phase flow.

The use of a data acquisition system or digital computer is beneficial to the practice of the present invention. A computer, in addition to taking readings from the various instruments and performing the requisite computations, may also be used to control the various valves and perform other regulatory tasks including iteratively varying the test fluid flow rate or supply pressure to perform a series of experiments at a given aperture setting.

BRIEF DESCRIPTION OF THE DRAWINGS

The actual construction, operation and the apparent advantages of the present invention will be better understood by referring to the drawings in which like numerals identify like parts and in which.

DESCRIPTION OF THE PREFERRED EMBODIMENT

Figure 1:
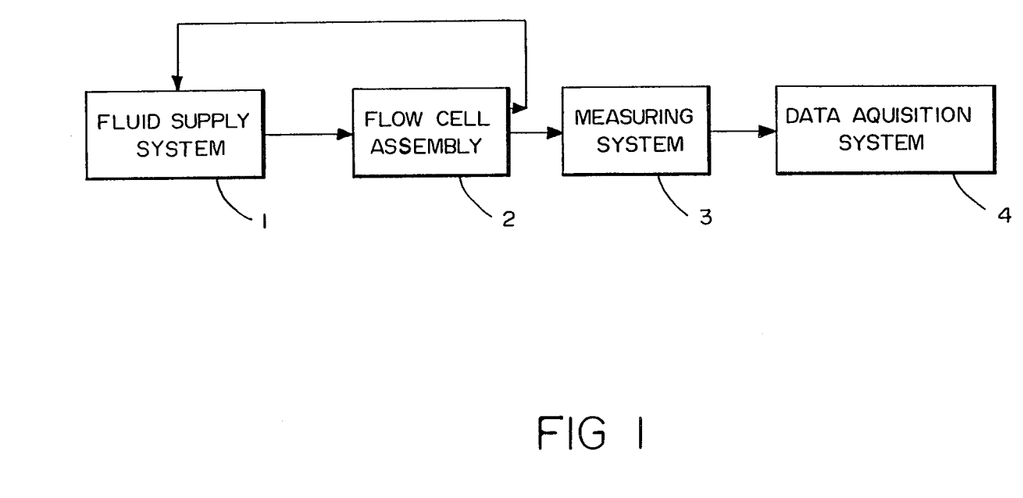
FIG. 1 is a block diagram of the system for measuring fluid flow parameters through naturally fractured media.

As shown in FIG. 1, which as with all figures presented herein is given by way of example and illustration and not of limitation, the apparatus of the present invention consists of four main sections: a fluid supply system 1, the flow cell assembly 2, measuring equipment 3 and a data acquisition system 4.

Figure 2:
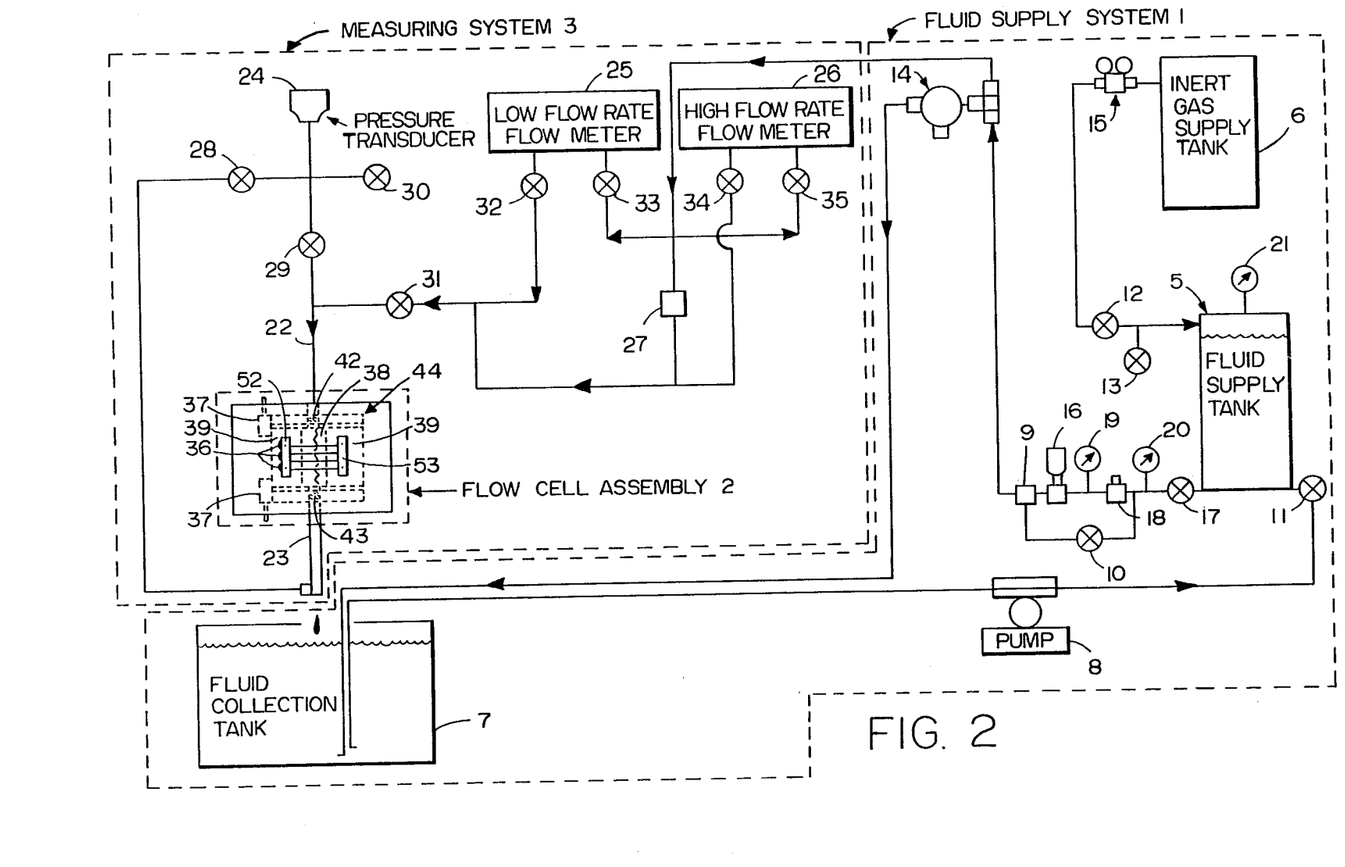
FIG. 2 is a schematic view of the present invention illustrating components of the apparatus as well as details of the fluid supply system.

FIG. 2 presents a detailed schematic representation of fluid supply system 1, flow cell assembly 2, and measuring equipment 3. As indicated in FIG. 2, the fluid supply system 1 includes the following: a fluid supply tank 5, an inert gas supply 6 for pressurizing the system, a fluid collection tank 7, recirculation pump 8, fluid control valves 9–13 and regulator valves 14–17. An inline filter 18 may be used at low flow rates. Pressure gages 19–21 monitor fluid supply conditions.

Flow cell assembly 2, which contains core assembly 44 and core sample blocks 38, is installed in the test system by connecting the inlet test fluid line 22 to the flow cell assembly's inlet port 42 and the outlet test fluid line 23 to the assembly's outlet port 43.

The measuring system 3 of the preferred embodiment is comprised of a pressure transducer 24, which may be a Heise Model 621 with a range of 0–100 psi, a low flow rate flow meter 25, which may be a micromotion Model D-6 with a range of 0 to 1 lb/min, a high flow rate flow meter 26 which may be a Micromotion Model D-12 with a range of 0 to 10 lb/min, a temperature sensor and readout 27 and flow control valves 28–35. Instrumentation used in the flow cell assembly 2 includes: three LVDTs 36 (Schaevitz High Resolution —5.5 mv with v/1000 microinch option) and two load cells 37 (Sensotec Model 31 subminature-style, 0–1000 lbs, type ¼-28 mnf). Outputs from these instruments may be fed into a data acquisition system or recorded manually.

The data acquisition system 4 of FIG. 1 used in the practice of the present invention is designed to collect test variable data upon request. The system is designed to permit all data collected during a test to be stored in the random access memory (RAM) of the computer. The data can then be recalled and processed by a mainframe computer, or by the data acquisition system computer itself. Key components of the data acquisition system of the preferred embodiment include a micro computer (IBM PC-AT with 30 megabit expansion board, or equivalent), a channel scanner (Kiethly 705 or equivalent) and a channel readout (Kiethly 195A digital multimeter or equivalent).

Figure 3:
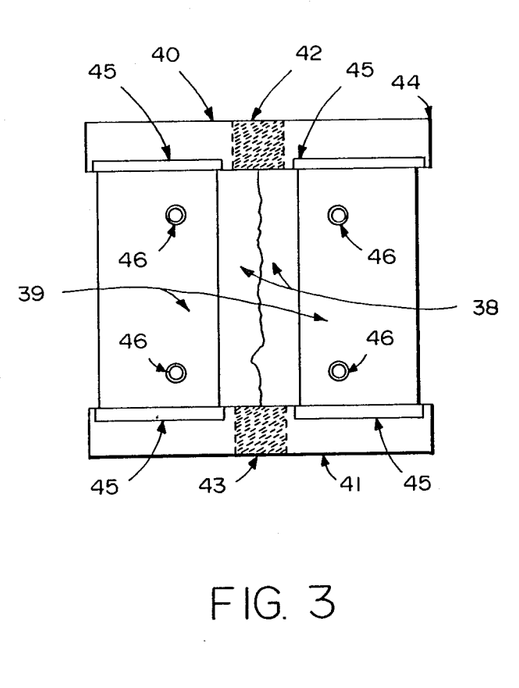
FIG. 3 is a top view of a core mounting assembly.

Referring now to FIG. 3, the core mounting assembly 44 will be described in detail. The pair of substantially rectangular core sample blocks 38, may be prepared from fractured base core material obtained from cored wells. Sandstone or chert are particularly desirable materials for the study of fracture flow in relatively non-porous materials, although any naturally fractured material is useful. Rectangular blocks are cut with large core cutting saws from the cylindrical cores so that the natural fractures in the cores are centered in the blocks; with mating fractured faces forming one side of each block. The blocks are then ground down to exact tolerances. A diamond-tipped griding machine is useful for this operation. All faces, with the exception of the fracture faces, must be parallel to assure a proper seal in the flow cell. One way to achieve this is to first cut two sides parallel and use a level to assure right angle cuts from the parallel side.

Figure 4:
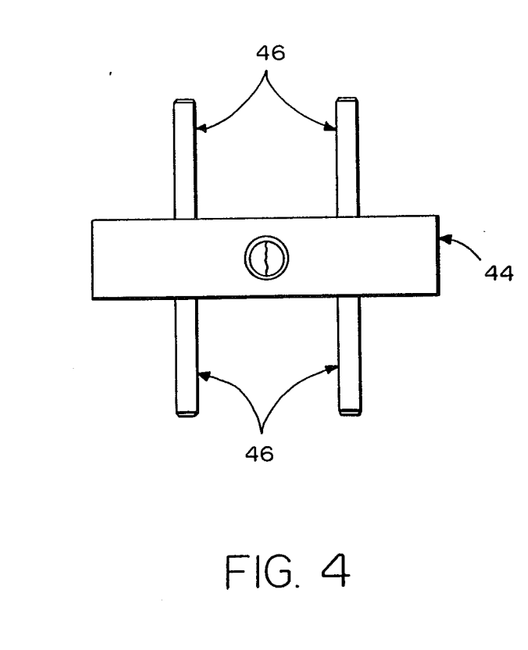
FIG. 4 is a front view of the core mounting assembly.

The finished core sample blocks are then dried and attached to core mounting blocks 39 using epoxy. A preferred material for fabricating the core mounting blocks is aluminum. An epoxy judged to be suitable for this application is BIPAX TRA-BOND BB-2143D, manufactured by Tra-Con, Inc. After applying the epoxy, the blocks are clamped together and left to cure for two days. Upon curing, they are machined down to their final size for use in the flow cell. The core sample blocks 38 and core mounting blocks 39 are placed between inlet and outlet end blocks 40 and 41, having inlet and outlet ports 42 and 43, also made of aluminum, to form the core assembly 44 used in the flow cell assembly 2. Gasketing is required to seal the end blocks 40 and 41 against the core mounting blocks 39 to prevent leakage. Teflon has proven to be a suitable material for forming gasket inserts 45. As shown in FIGS. 3 and 4, four pins 46, preferably made of steel, are then pressed into each aluminum core mounting block for use in monitoring core movement during testing.

Figure 5:
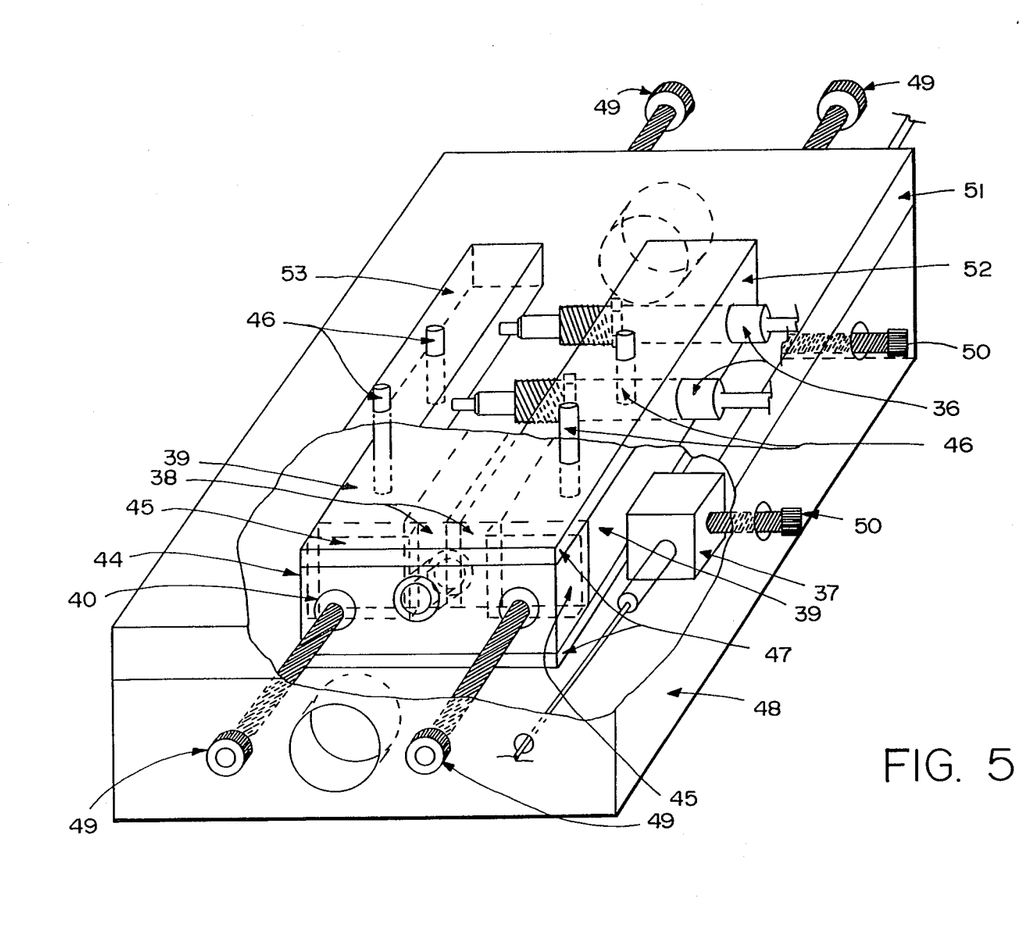
FIG. 5 is a cut-away view in perspective of the assembled flow cell of the present invention.

Reference is made now to FIG. 5 in which the flow cell assembly is shown. Two gaskets 47 are cut to the shape of the aluminum/rock core pieces already fabricated. A useful gasket material is polyurethane with a durometer hardness, as measured by ASTM D-2240, of about 60A. As shown, they are used as the top and bottom seals for the core assembly 44. The core assembly 44 is installed along with the bottom gasket 47 into the core assembly housing 48. The fracture aperture is set to the desired width and the inlet end block 40 and the outlet end block (not shown) are secured to fix the aperture by tightening set screws 49. The load cell set screws 50 are set as desired and the top gasket 47 and core assembly housing top plate 51 installed.

Figure 6:
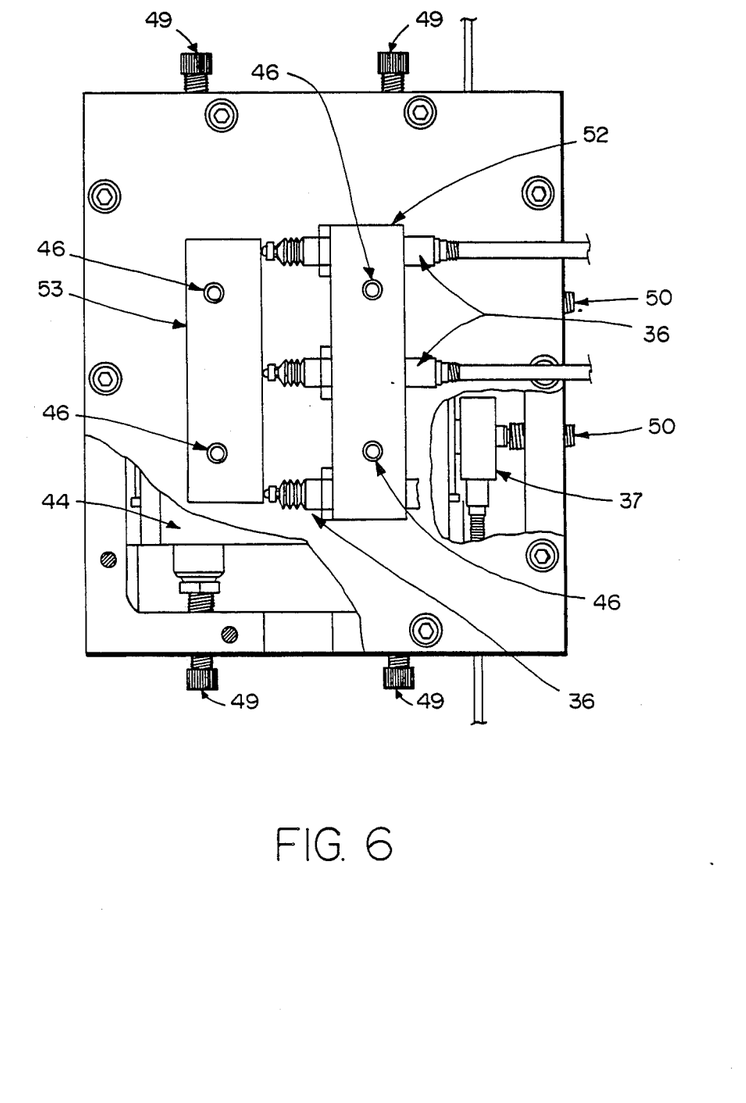
FIG. 6 is a cut-away view from the top of the assembled flow cell.

Refer now to FIG. 6 for further description of the flow cell assembly. The three linear variable differential transformers (LVDTs) 36 shown mounted on the top of the flow cell assembly are useful in monitoring core sample block movement during testing. The LVDTs are used by mounting them within a holder 52 and installing this assembly and a reference block 53 on the protruding dowel pins 46.

Figure 7:
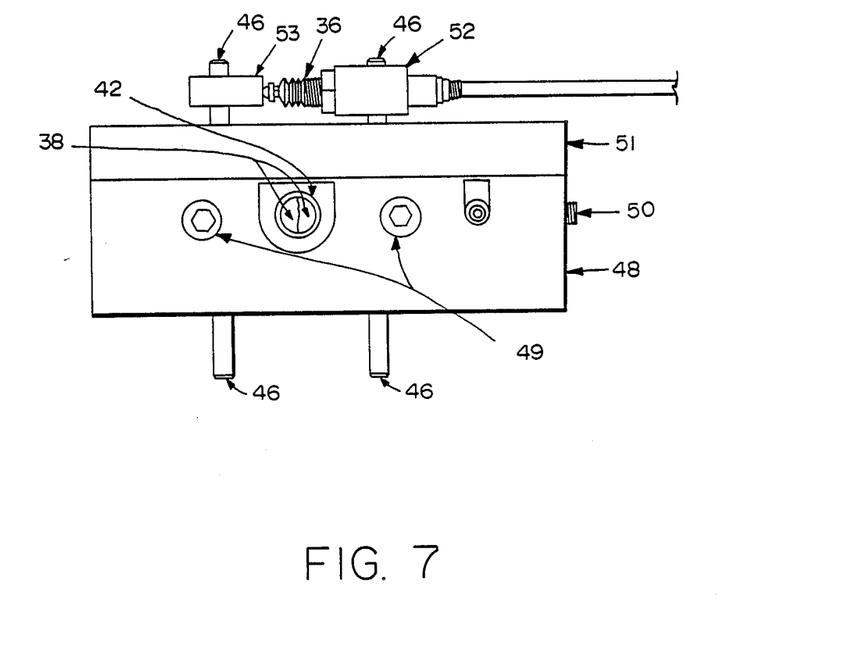
FIG. 7 is a front view of the flow cell assembly.
Figure 8:
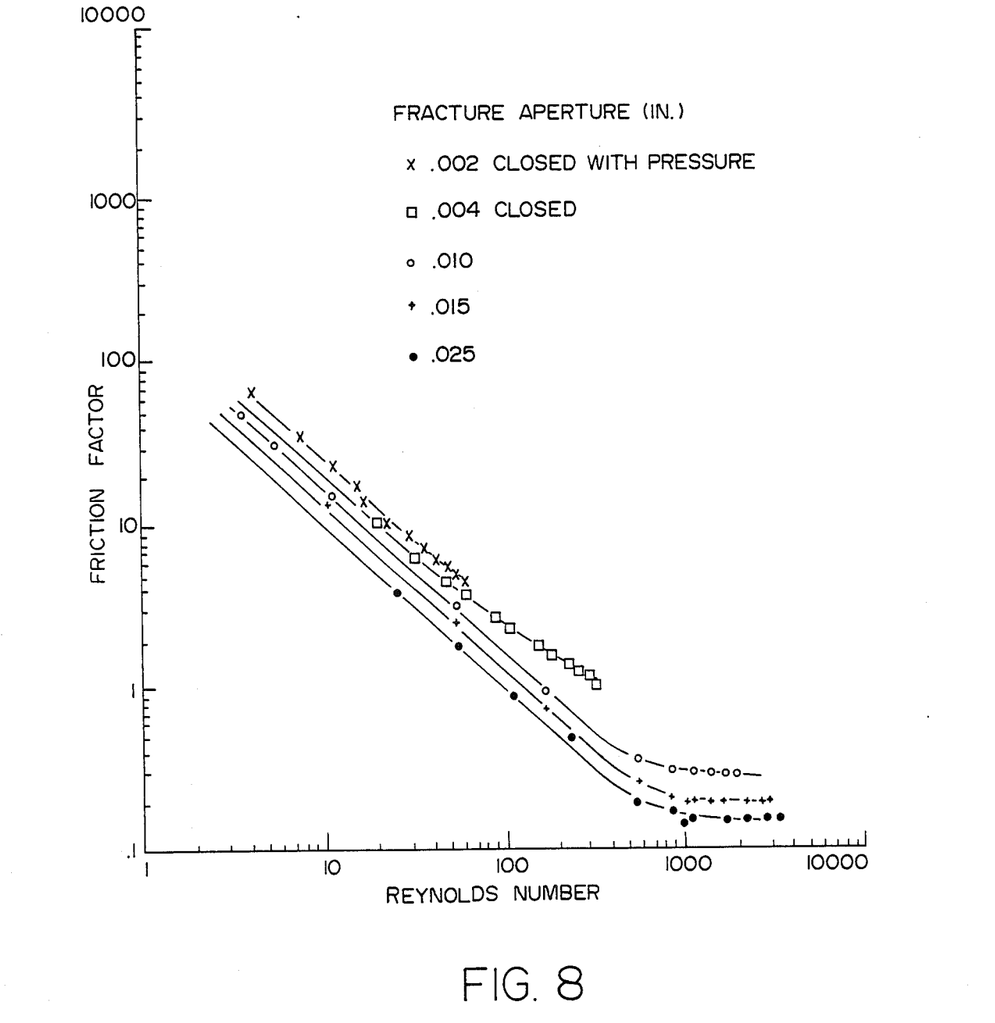
FIG. 8 is a graph illustrating the dependence of friction factor and Reynolds number upon fracture aperture and surface roughness.

As shown in FIG. 7, when assembled, the fracture faces are aligned with the inlet and outlet ports of the flow cell assembly. Pictures may be taken through the inlet and outlet end pieces 40 and 41 using a long distance microscope to accurately establish the fracture aperture.

EXAMPLE

The following example is illustrative of the present invention:

The naturally fractured core sample blocks 38 and aluminum core sample mounting blocks 39 were prepared as described above. The fracture faces were rinsed and the mounted core blocks placed in the flow cell housing 48 with bottom gasket 47 in place. The two load cells 37 were installed next. The fracture faces of the core sample blocks 38 were moved together until the fracture was closed. The inlet and outlet end pieces 40 and 41, respectively, were next installed and hand tightened. The load cell set screws 50 were tightened next until 100 lbs. registered on each cell. (This was used as a zero reference fracture setting for fracture aperture measurement.) Next, the LVDTs 36 were placed on pins 46 protruding from the top of the core mounting blocks 39 (the core assembly housing top plate 51 was not on at this point). LVDT readings were recorded. This procedure was repeated using the bottom pins 46. (Readings were taken while the core cell is on its side.) After taking the pressure off load cells 37, LVDTs 36 were removed and the inlet and outlet end pieces 40 and 41 loosened. The desired fracture aperture was then set and end pieces 40 and 41 retightened to 20 in. lbs. Next, top gasket 47 and the core assembly housing top plate 51 were installed. With a torque wrench, all top bolts were tightened to 20 in. lbs., taking care to alternate bolts from side to side to maintain a uniform pressure on the top plate. Next the inlet and outlet end pieces 40 and 41 were tightened to 40 in. lbs. by alternating bolts until the desired force was reached. LVDTs 36 were reinstalled and readings taken as before for the fracture set points. The differences between the first readings and the second readings were equated to rough estimates of the respective apertures of the fracture. Several pictures were taken of the fracture through the inlet and outlet end pieces 40 and 41 using a long distance microscope. These pictures were used to obtain an average fracture aperture value for computational purposes. The flow cell was then attached to the inlet and outlet lines of the fluid supply system.

Referring back now to FIG. 2, the fluid supply vessel 5 was filled using the fluid pump 8. Valves 11, 13 and 17 were then closed and the fluid supply vessel 5 pressurized with nitrogen supplied from tank 6. Next, the appropriate mass flow meter 25 or 26 was selected and valves 32, 33, 34 and 35 adjusted accordingly. Flow meter 25 was used for flows between 0.002 and 1.0 lb/min; with flow meter 26 used for flows between 1.0 and 6.5 lb/min. Atmospheric pressure (pressure on the outlet side of the core) was determined next by the following procedure:

(a) Open valves 28, 29 and 30 and flow air into 30 to remove any intrained water present in the pressure bypass line.
(b) Close valves 29 and 30. This reading is the atmospheric pressure reading (zero pressure reading) used to obtain the differential pressure across the fracture.
(c) Check the zero pressure reading by opening valve 30. If the readings do not correspond, repeat step (a). This procedure assures that no fluid pressure head error is experienced during low flow data collection.
(d) Close valves 28 and 29 and open 30. The system is now ready to run.

The test was begun by slowly filling the system with water until all lines and the fracture were liquid-filled by the opening of valves 9, 16 and 17. Flow rates were controlled through the use of valves 16 and 17. The data acquisition system 4 was setup to collect data. Data collection was begun at low flow rates first. The pressure was increased slowly to obtain the required data. The back pressure regulator 14 was used during testing when the pressure was not stable (generally under 10 psi).

The above steps were repeated at several aperture settings for the same core sample. These were 0.002 in. (closed with pressure), 0.004 in. closed without pressure, 0.010 in., 0.015 in. and 0.025 in. Reynolds number and friction factors were computer from the data obtained. These are graphically depicted in FIG. 7.

The invention and its broader aspects is not limited to the specific details shown and described. Although the invention has been described with preferred embodiments, it is to be understood that modifications and variations may be made without departing from the spirit and scope of the invention as those skilled in the art will readily understand.

We claim:

1. An apparatus for the study of fluid flow through naturally fractured media, comprising:
   (a) a flow cell assembly for passing a test fluid through naturally fractured media having a housing for mounting the media within;
   (b) means for mounting the naturally fractured media within said housing so that the fracture is aligned to permit the test fluid to be introduced substantially parallel to the fracture; and
   (c) means for permitting adjustment of an aperture formed by the fracture so that varied apertures may be established.

2. The apparatus of claim 1, wherein said mounting means comprises: first and second core mounting blocks for affixing thereto a pair of core sample blocks prepared from the naturally fractured media having naturally fractured faces; and an inlet end block and an outlet end block each having a fluid flow port and a surface conducive to sealing for inserting said first and second core mounting blocks and core sample blocks therebetween to form a core assembly.

3. The apparatus of claim 2, wherein said flow ports of said end blocks are in mutual general axial alignment with each other and with the fracture aperture.

4. The apparatus of claim 3, further comprising means of accurately measuring the fracture aperture by high magnification photography.

5. The apparatus of claim 2, wherein said sealing surfaces contact said first and second core mounting blocks to prevent leakage.

6. The apparatus of claim 5, wherein said surfaces conducive to sealing of said inlet and outlet end blocks are teflon gasket inserts.

7. The apparatus of claim 1, wherein said flow cell assembly has a removable top.

8. The apparatus of claim 7, wherein said flow cell assembly housing has an upward facing sealable surface and said removable top has in inward facing sealable surface to prevent leakage.

9. The apparatus of claim 8, wherein said sealable surfaces of said flow cell assembly housing are provided through the use of gasket material.

10. The apparatus of claim 9, wherein said gasket material is polyurethane having a durometer hardness of about 60A.

11. The apparatus of claim 1, further comprising means for measuring core sample loading.

12. The apparatus of claim 11, wherein said means for measuring core sample loading comprises at least one electronic load cell.

13. The apparatus of claim 1, further comprising means for measuring core sample displacement during testing.

14. The apparatus of claim 13, wherein said means for measuring sample displacment comprises at least one linear variable differential transformer.

15. The apparatus of claim 1, further comprising means for providing a regulated flow of test fluid.

16. The apparatus of claim 15, wherein said means for providing a regulated flow of test fluid is a pressurized recirculatory fluid system.

17. The apparatus of claim 16, wherein pressurization is provided by an inert gas.

18. The apparatus of claim 15, further comprising means for measuring fluid flow through the fracture aperture.

19. The apparatus of claim 15, further comprising means for measuring the pressure drop across the fracture aperture resulting from the flow of fluid through the aperture.

20. The apparatus of claim 1, further comprising means to acquire, store and process test data.

21. A method for measuring fluid flow through naturally fractured media, comprising the steps of:
   (a) mounting a naturally fractured media sample within a flow cell assembly having inlet and outlet ports;
   (b) setting a fracture aperture;
   (c) introducing a testing fluid under pressure into said inlet port of said flow cell contacting the naturally fractured media and thereafter exiting through said outlet port of said flow cell assembly; and
   (d) measuring at least one fluid flow parameter resulting from the flow of said testing fluid through said flow cell.

22. A method as recited in claim 21, wherein said fluid flow parameter is flow rate.

23. A method as recited in claim 22, wherein the step of measuring at least one fluid flow parameter further includes measuring a pressure drop across said flow cell assembly resulting from the flow of said testing fluid through said flow cell assembly.

24. A method as recited in claim 21, wherein said fluid flow parameter is pressure drop.

25. A method as recited in claim 21, wherein the step of introducing a testing fluid and contacting said naturally fractured media includes contacting said media substantially parallel to said mating fracture faces.

26. A method as recited in claim 21, further comprising the step of regulating a supply of fluid for introducing into said inlet port of said flow cell assembly so as to provide fluid at substantially constant temperature and pressure.

27. A method as recited in claim 21, further comprising:
(f) changing the pressure under which said fluid is introduced into said inlet port of said flow cell assembly and repeating step (e).

28. A method as recite in claim 27, further comprising:

(g) repeating step (f) a plurality of times.

29. A method as recited in claim 28, wherein steps (d)–(g) are digitally controlled.

30. A method as recited in claim 28, further comprising:
(h) resetting the fracture aperture and repeating steps (d)–(g).

31. A method as recited in claim 30, further comprising the step of repeating step (h) at least once.

32. A method according to claim 21, further comprising the step of reading and storing measured fluid flow data through the use of a computerized data acquisition unit.

33. A method according to claim 21, wherein the test fluid is a single-phase fluid.

34. A method according to claim 21, wherein the test fluid is a multi-phase fluid.

35. A method according to claim 21, further comprising the step of accurately measuring the fracture aperture insitu by high magnification photography.

* * * * *